US012662681B2

(12) United States Patent
Sixto et al.

(10) Patent No.:  US 12,662,681 B2
(45) **Date of Patent:  \*Jun. 23, 2026**

(54) MULTI-PULSE TRANSFECTION METHODS AND CELLS

(71) Applicant: NantBio, Inc., Culver City, CA (US)

(72) Inventors: Marcos Sixto, Culver City, CA (US);
Kayvan Niazi, Culver City, CA (US);
Ting Wu, Culver City, CA (US);
Chihwei Chang, Culver City, CA (US)

(73) Assignee: NantBio, Inc., Culver City, CA (US)

( * ) Notice:  Subject to any disclaimer, the term of this patent is extended or adjusted under 35 U.S.C. 154(b) by 151 days.

This patent is subject to a terminal disclaimer.

(21) Appl. No.: 18/587,120

(22) Filed:  Feb. 26, 2024

(65)  Prior Publication Data

US 2024/0209384 A1   Jun. 27, 2024

Related U.S. Application Data

(63) Continuation of application No. 16/903,971, filed on Jun. 17, 2020, now Pat. No. 11,939,585, which is a continuation of application No. 15/727,150, filed on Oct. 6, 2017, now Pat. No. 10,724,043.

(60) Provisional application No. 62/404,993, filed on Oct. 6, 2016.

(51) Int. Cl.
| | |
|---|---|
| *C12N 15/85* | (2006.01) |
| *C12N 5/10* | (2006.01) |
| *C12N 15/82* | (2006.01) |
| *C12N 15/87* | (2006.01) |
| *A61K 48/00* | (2006.01) |

(52) U.S. Cl.
CPC ........... *C12N 15/8206* (2013.01); *C12N 5/10* (2013.01); *C12N 15/85* (2013.01); *C12N 15/87* (2013.01); *A61K 48/00* (2013.01)

(58) Field of Classification Search
CPC ...... C12N 15/8206; C12N 5/10; C12N 15/85; C12N 15/87; A61K 48/00
See application file for complete search history.

(56)  References Cited

U.S. PATENT DOCUMENTS

| | | | |
|---|---|---|---|
| 5,789,213 A | 8/1998 | Hui et al. | |
| 5,945,292 A | 8/1999 | Brizzard et al. | |
| 6,603,998 B1 | 8/2003 | King et al. | |
| 9,488,637 B2 | 11/2016 | Gillis et al. | |
| 2003/0073238 A1 * | 4/2003 | Dzekunov ............ | A61K 9/5068 |
| | | | 435/173.6 |
| 2005/0221493 A1 | 10/2005 | Vogels et al. | |
| 2008/0076144 A1 | 3/2008 | Ragsdale | |
| 2010/0049372 A1 | 2/2010 | Ragsdale | |
| 2012/0190583 A1 | 7/2012 | Gillis et al. | |
| 2017/0065636 A1 | 3/2017 | Moriarity et al. | |
| 2018/0016539 A1 | 1/2018 | Ding et al. | |

| | | | |
|---|---|---|---|
| 2018/0171298 A1 | 6/2018 | Duchateau et al. | |
| 2018/0236053 A1 | 8/2018 | Dusseaux | |
| 2019/0336529 A1 | 11/2019 | Inderberg et al. | |

FOREIGN PATENT DOCUMENTS

| | | | | | |
|---|---|---|---|---|---|
| AU | 2011281121 A1 * | 2/2013 | ......... | G01N 33/5035 |
| WO | WO-2005032646 A2 | 4/2005 | | |
| WO | WO-2017194555 A1 | 11/2017 | | |

OTHER PUBLICATIONS

Kubiniec et al in "Effects of pulse length and pulse strength on transfection by electroporation" Biotechniques Jan. 1990 vol. 8, No. 1. pp. 16-20 (Abstract only). (Year: 1990).*
Takahashi et al in "Cytoplasmic expression of EGFP in dendritic cells transfected with in vitro transcribed mRNA or cellular total RNA extracted from EGFP expressing leukemia cells" (Medical Oncology 2003 vol. 20, pp. 335-348). (Year: 2003).*
Schoenberg et al., "Chapter 11 Delivery of DNA into Natural Killer Cells for Immunotherapy", pp. 165-172 of S. Li (ed.), Electroporation Protocols: Preclinical and Clinical Gene Medicine. from Methods in Molecular Biology, vol. 423. Humana Press (2008). (Year: 2008).
Heiser, W. C., "Optimizing Electroporation Conditions for the Transformations of Mammalian Cells," Springer Nature, Transcription Factor Protocols, Methods in Molecular Biology™, 130: 117-134 (2000).
Office Action issued in U.S. Appl. No. 15/727,150 dated Sep. 20, 2018.
Office Action issued in U.S. Appl. No. 15/727,150 dated Apr. 2, 2019.
Office Action issued in U.S. Appl. No. 15/727,150 dated Oct. 21, 2019.
Notice of Allowance issued in U.S. Appl. No. 15/727,150 dated Apr. 2, 2020.
Supplemental Notice of Allowance issued in U.S. Appl. No. 15/727,150 dated May 6, 2020.
Boissel et al. (2009). Transfection with mRNA for CD19 specific chimeric antigen receptor restores N K cell mediated killing of CLL cells. Leuk Res, 33(9): 1255-1259.
Paganin-Gioanni et al. (2011). Direct visualization at the single-cell level of siRNA electrotransfer into cancer cells. PNAS, 108: 10443-10447.
Stroh et al. (2010). Combined Pulse Electroporation—A Novel Strategy for Highly Efficient Transfection of Human and Mouse Cells. PloS One, 5(3): 1-8.
Methods in Molecular Biology, (1995). Animal Cell Electroporation & Electrofusion Protocols. Human Press, Inc., 48: 3-369.
Kubiniec et al. (1990). Effects of pulse length and pulse strength on transfection by electroporation. Biotechniques, 8(1): 16-20.
Office Action issued in U.S. Appl. No. 16/903,971 dated Jul. 22, 2022.

(Continued)

*Primary Examiner* — Catherine S Hibbert
(74) *Attorney, Agent, or Firm* — Harness Dickey & Pierce P.L.C.

(57)  ABSTRACT

Systems and methods are provided for transfecting immune competent cells with RNA at high efficiency and viability.

17 Claims, 2 Drawing Sheets

(56)                 References Cited

OTHER PUBLICATIONS

Office Action issued in U.S. Appl. No. 16/903,971 dated Feb. 9, 2023.
Office Action issued in U.S. Appl. No. 16/903,971 dated Jun. 22, 2023.
Notice of Allowance issued in U.S. Appl. No. 16/903,971 dated Nov. 17, 2023.

* cited by examiner

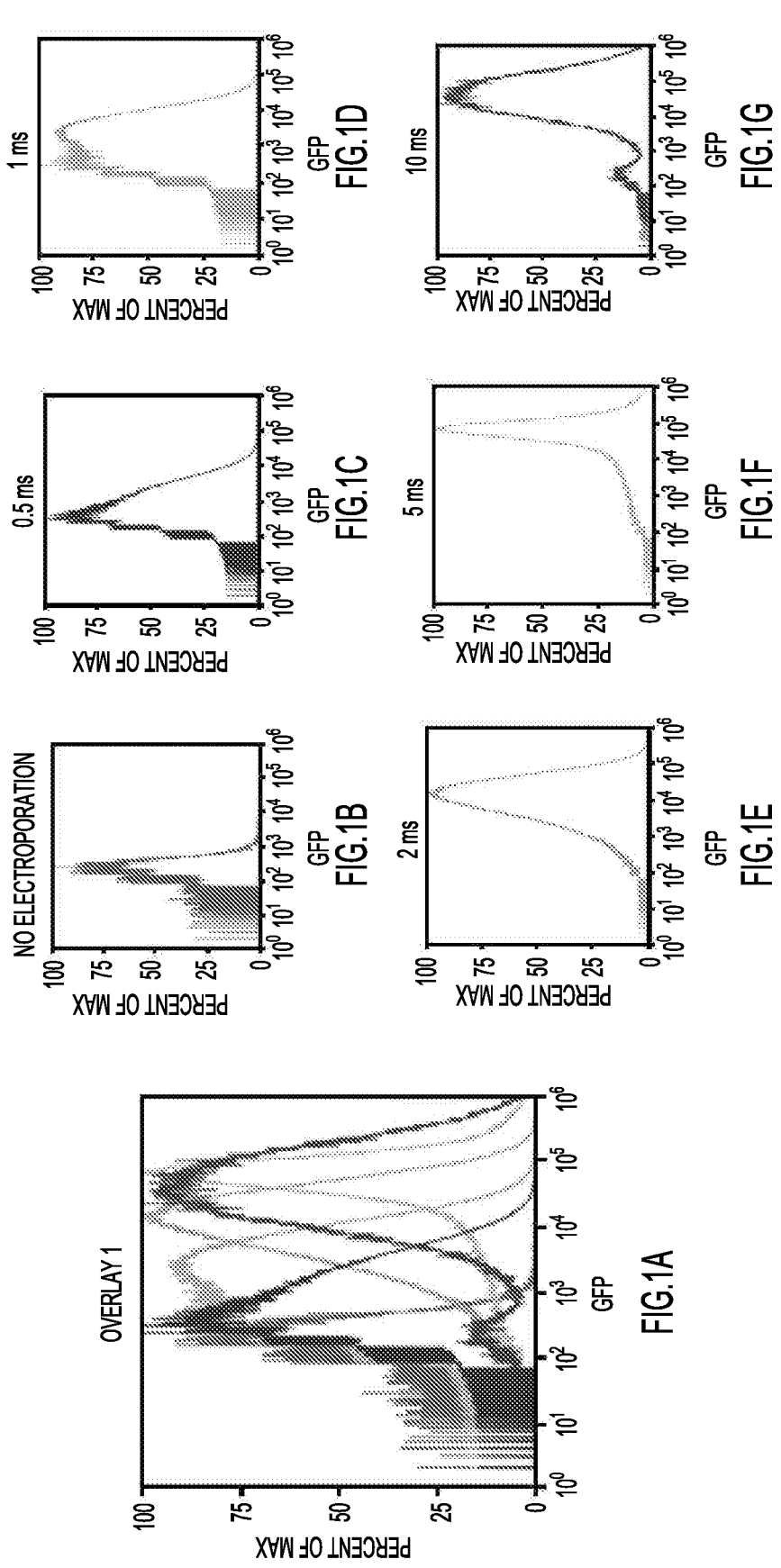

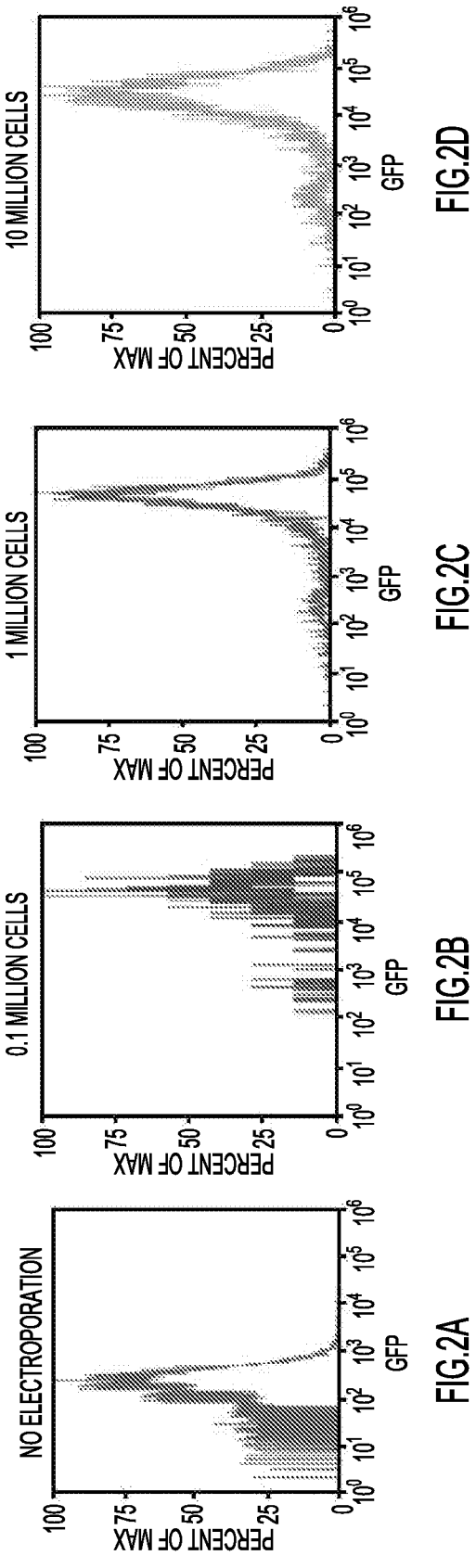

MULTI-PULSE TRANSFECTION METHODS AND CELLS

CROSS-REFERENCE TO RELATED APPLICATIONS

This application is a continuation of U.S. Patent Application Ser. No. 16/903,971 filed on 17 Jun. 2020, which is a continuation of U.S. Patent Application Ser. No. 15/727,150 filed on 6 Oct. 2017, now U.S. Pat. No. 10,724,043 issued on 28 Jul. 2020, which claims the benefit of U.S. Provisional Patent Application Ser. No. 62/404,993, filed on 6 Oct. 2016. The entire disclosures of each of the above recited applications are incorporated herein by reference.

FIELD OF THE INVENTION

The field of the invention is transfection systems and methods for electroporation of cells, and especially NK cells.

BACKGROUND OF THE INVENTION

The background description includes information that may be useful in understanding the methods and techniques presented herein. It is not an admission that any of the information provided herein is prior art or relevant to the subject matter presented herein, or that any publication specifically or implicitly referenced is prior art.

Electroporation is a well-known technology used to transfect a wide variety of cell types, typically with nucleic acid molecules, using application of a controlled direct current (DC) electrical pulse for a relatively short duration of time. The pulse is thought to induce a transmembrane potential that causes a reversible breakdown of the ordered structure of a cell membrane, leading to the formation of pores in the membrane. Molecules of interest can then enter the cell through the pores until the pores close, typically within milliseconds to seconds. Pore formation can be controlled by adjusting various parameters, especially gap width, pulse wave form, field strength, temperature, and pulse length.

While there are various known electroporation parameters for commonly used cells, there is a lack of predictability for specific electroporation parameters for other types of cells. Indeed, most electroporation protocols will give only large ranges for parameters. For example, mammalian cell electroporation is typically performed at field strengths between 0.25-3 kV/cm, with a voltage of 100-500 V and using a 4 mm cell gap for cells having a diameter between 10-50 microns. In the vast majority of cases, single pulse electroporation is typically performed. Although modification of the pulse number has been described (e.g., BTX Online, General Optimization Guide for Electroporation), specific parameters were not provided aside from a generic recommendation to use very low voltages (10-100V) with pulse lengths ranging between 30-50 msec. In another case, multiple pulses were described for uptake of FITC-dextran into yeast at a field strength of at least 3 kV/cm. Here, increased pulse number correlated with increased uptake, albeit at decreased viability.

Various NK cells have been transfected using mRNA and electroporation, for example, to genetically manipulate primary NK cells to express CARs (*Leuk Res.* 2009 September; 33(9): 1255-9) or to express cytokines for autocrine growth stimulation (*Cytotherapy* (2008) 10:265-74). With technological advances and the use of mRNA instead of cDNA, transfection efficiencies have increased dramatically, reaching up to 90% or more while having only a minimal deleterious effect on cell viability (*Front Immunol.* 2015; 6: 266). Notably, using mRNA electroporation, transfection efficiencies of 80-90% can be achieved in not only ex vivo expanded cells but also in primary resting non-cytokine activated human NK cells (*Cancer Gene Ther* (2010) 17:147-54). Despite this remarkable advance, a detailed characterization on the effects of electroporation on the phenotype, function, and proliferative capacity of NK cells following electroporation is not generally known. Moreover, viability of the transfected cells is often less than desirable and there appears to be a trade-off between transfection efficiency and viability.

Thus, even though various transfection systems and methods for mammalian cells, including NK cells, are known in the art, all or almost all of them suffer from one or more disadvantages. Therefore, there is still a need to provide improved electroporation systems and methods.

SUMMARY

The techniques presented herein are directed to various devices, systems, and methods for electroporation of mammalian cells, and especially immune competent cells (e.g., NK cells, T-cells, B-cells, macrophages, etc.). More specifically, the inventors have discovered a range of electroporation conditions that allow for transfection of immune competent cells with RNA at a high efficiency and at high viability of the transfected cells.

Various objects, features, aspects and advantages of the inventive subject matter will become more apparent from the following detailed description of preferred embodiments, along with the accompanying drawing figures in which like numerals represent like components.

BRIEF DESCRIPTION OF THE DRAWINGS

FIGS. 1A-1G show transformation efficiencies using various time constants, according to the techniques presented herein.

FIGS. 2A-2D show transformation efficiencies at various cell concentrations, according to the techniques presented herein.

DETAILED DESCRIPTION

The inventors have discovered systems and methods of transfection of mammalian cells, and especially immune competent cells (e.g., NK cells, T-cells, B-cells, macrophages, etc.) using an electroporation protocol in which the cells are subjected to multiple pulses at a moderate voltage, a small gap width, relatively moderate capacitance, and a short time constant.

In general, the inventors have discovered that immune competent cells, and especially NK cells, can be transfected with RNA (e.g., synthetic RNA, mRNA, in vitro transcribed RNA, etc.) using multi-pulse conditions using a very short time constant, typically a time constant of less than 10 msec, or even more typically of less than 5 msec. For example, the time constant may range from about 0.5 to 10 ms, from about 1 to 5 ms, and from about 1 to 4 msec; most typically the time constant is between 1-3 msec. Such conditions are generally achieved using a cell gap of 0.2 cm and a voltage of about 200V. Viewed from another perspective, the field strength of electroporation is typically between about 800 V/cm and 1200 V/cm. However, lower field strengths (e.g., about 600-800 V/cm, or about 400-600 V/cm) and higher field strengths (e.g., about 1,000-1,400 V/cm) are also contemplated. Therefore, the gap width need not be limited to 0.2 cm, but may also range from about 0.1 cm to 0.4 cm. The amount of mRNA added to the electroporation reaction may be about 600 ng, about 1000 ng, or more.

With respect to suitable capacitance, it is contemplated that the capacitance should be relatively moderate, typically about 10 µF, and more typically about 25 µF. Viewed form a different perspective, suitable capacitance settings will be between about 1 to 150 µF or about 1-100 µF, and more typically between about 5-75 µF, or about 5-50 µF, about 10 to 40 µF, or about 20-30 µF. Both high voltage with low capacitance (short pulse duration) or low voltage with high capacitance (long pulse duration) have previously been used to achieve successful gene transfer (*Nucl Acids Res.* 1987; 15:1311-1326). Notably, the present systems and methods use a low voltage moderate capacitance setting to achieve high transfection efficiency at high viability in a relatively conductive electroporation medium.

With respect to suitable pulse numbers and pulse-to-pulse intervals, the inventors noted that at least two, three, and in some cases four pulses provided more desirable results than a single pulse or of five or more pulses. Therefore, it is contemplated that a preferred pulse number is between 2-4 pulses. Most typically, the pulses are separated from subsequent pulses by a relatively short interval, typically between 1 second and 15 seconds, and in some cases even longer. However, interval lengths of between 2-10 seconds are generally preferred.

In further contemplated aspects, the medium in which the cells are transfected is an isotonic medium, optionally containing one or more nutrients. Therefore, and viewed from a different perspective, suitable media include growth media (with or without serum), and especially RPMI, MEM, and DMEM. In some aspects, the medium is RPMI, a high-conductivity medium, wherein the conductivity of RPMI is about 1370 mS/m. Media also may include minimal media and Ringer's solution. Thus, it should be noted that the media are generally electrically conductive media. In other aspects, the medium may also be sterile (and in some cases non-isotonic) non- or low-conductance solutions.

EXAMPLES

Example 1. Materials

Materials included a 0.2 cm electroporation cuvette (VWR Cat #89047-208); RPMI 1640, Corning (VWR Cat #45000-396); GenePulser 2 Bio Rad with Gene Pulse Controller II and capacitance extender Plus Connected in the High Voltage position ("bacterial setting"); XVIVO 10 NK complete media (Lonza Cat #04-743Q); and mRNA at high concentration [above 1 ug/ul] (Anti Reverse Cap Analog-Trilink Cat #N-7003, T7 High Scribe NEB-E2040S).

Example 2: Protocol for mRNA Electroporation into hANKs

Obtained 10M cells per electroporation and transferred to a suitable conical centrifuge tube, then spun cells down at 400×g for 5 minutes and aspirated media. While cells were spinning, 5-10 mL of XVIVO 10 Nk complete media was added to a T-25 flask upright and incubated in a 5% $CO_2$ and 37° C. incubator for 10-25 minutes until the medium had equilibrated. Cells were washed with 5 mL RPMI 1640 and re-suspended, then cells were spun down at 400×g for 5 minutes. Into a 0.2 cm cuvette, 2.5 µg of each mRNA to be transformed was added. The RPMI 1640 was aspirated from the cells and the cells were re-suspended with 30 µl of RPMI 1640. 50 µl of the hANK+RPMI 1640 mixture was added to the 0.2 cm cuvette containing mRNA. The cuvette was shaken until the content settled to the bottom of the cuvette. The Gene Pulser II was set with 200 Ohm resistance, 25 µF capacitance, and 200V voltage. The sample was pulsed 3 times, with about 5 seconds between the pulses. The time constant was between 1.5-2.5 milliseconds. After electroporation, the hANKS were transferred to the T-25 flask for incubation. The remaining cells in the cuvette were washed with media and transferred to the T-25 flask. Cells were incubated overnight.

Example 3: Results

Using the above parameters, the inventors noted viability of the NK cells above 80% at a transfection efficiency (based on GFP capped mRNA) above 70%.

Example 4: Optimization of the Time Constant and Injected Charge

Further experiments were conducted to determine the optimal time constant and injected charge. For these experiments, the following setup conditions were used:

at a time constant of 0.5 ms, 100 ohm and 10 µF were used;

at a time constant of 1 ms, 1000 ohm and 10 µF were used;

at a time constant of 2 ms, 200 ohm and 25 µF were used;

at a time constant of 5 ms, 200 ohm and 75 µF were used; and at a time constant of 10 ms, 200 ohm and 150 µF were used (in duplicate pool after electroporation).

Table 1 shows that for the conditions tested, 2 ms was the optimal time constant, and 5 mC was the optimal injected charge. Thus, the injected charge may range from about 1 mC to about 30 mC, from about 2 mC to about 15 mC, from about 3 mC to 10 mC, from about 4 mC to about 8 mC, from about 4 mC to 6 mC, or may optimally be about 5 mC. For each electroporation, the following conditions were also used: 200V, 600 ng of mRNA GFP, and an average final volume of about 50 ul in RPMI, with a 2 mm cuvette.

TABLE 1

| Time constant | Amount of injected charge | Average current | RNA transfection efficiency in live cells | Cell Viability | RNA transfection efficiency in total cells |
|---|---|---|---|---|---|
| 0.5 ms | 2 mC | 2.5 A | 34% | 81% | 27.5% |
| 1 ms | 2 mC | 1.3 A | 51% | 91% | 46.4% |
| 2 ms (optimal) | 5 mC | 1.6 A | 84% | 85% | 71.4% |
| 5 ms | 15 mC | 1.9 A | 78% | 68% | 53.0% |
| 10 ms | 30 mC | 1.9 A | 89% | 62% | 55.2% |

An optimal time constant of 2 ms was selected, as this time constant maintained the highest combination of RNA transfection efficiency (84%) and highest cell viability (85%). Table 1 also shows the corresponding optimal injected charge of about 5 mC.

FIGS. 1A-1G show GFP expression for populations of cells at different time constants. FIG. 1A is an overlay of FIGS. 1B-1G. Here, the efficacy of expression of GFP (as a percentage of maximum) is shown to be optimal at about 5 ms.

Example 5: Effect of Cell Density on Electroporation Efficiency

Further experiments were conducted to determine the relationship of cell density to electroporation efficiency. For these experiments, the following setup conditions were used: a time constant of 2 ms, 200 ohm and 25 μF (in duplicate pools kept separate after electroporation). Each electroporation run also included the following conditions: 200 V, 1000 ng of mRNA GFP, and an average final volume of about 50 ul in RPMI, using a 2 mm cuvette.

This protocol was tested on 30 M cells, 10 M cells, 1 M cells, and 0.1 M cells. Table 2 summarizes the results.

TABLE 2

| Cell number in 50 ul reaction volume | RNA transfection efficiency in live cells |
|---|---|
| 0.1 million | 89% |
| 0.1 million | 93% |
| 1 million | 92% |
| 1 million | 93% |
| 10 million | 91% |
| 10 million | 80% |

Table 2 shows that the electroporation protocol was not sensitive to cell density over a range of 0.1 million to 10 million cells in a 50 ul reaction volume. FIGS. 2A-2D show that GFP expression (as a percent of maximum) stayed about the same as cell density increased.

In some embodiments, the numbers expressing quantities of ingredients, properties such as concentration, reaction conditions, and so forth, used to describe and claim certain embodiments are to be understood as being modified in some instances by the term "about." Accordingly, in some embodiments, the numerical parameters set forth in the written description and attached claims are approximations that can vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments are approximations, the numerical values set forth in the specific examples are reported as precisely as practicable. The numerical values presented in some embodiments may contain certain errors necessarily resulting from the standard deviation found in their respective testing measurements.

As used in the description herein and throughout the claims that follow, the meaning of "a," "an," and "the" includes plural reference unless the context clearly dictates otherwise. Also, as used in the description herein, the meaning of "in" includes "in" and "on" unless the context clearly dictates otherwise. Unless the context dictates the contrary, all ranges set forth herein should be interpreted as being inclusive of their endpoints, and open-ended ranges should be interpreted to include commercially practical values. Similarly, all lists of values should be considered as inclusive of intermediate values unless the context indicates the contrary.

It should also be apparent to those skilled in the art that many more modifications besides those already described herein are possible without departing from the inventive concepts herein. Moreover, in interpreting both the specification and the claims, all terms should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. Where the specification claims refers to at least one of something selected from the group consisting of A, B, C . . . and N, the text should be interpreted as requiring only one element from the group, not A plus N, or B plus N, etc.

What is claimed is:

1. A method of transfecting mammalian cells with a RNA, comprising:

disposing the mammalian cells with the RNA in a transfection medium, wherein the mammalian cells are NK cells;

applying two, three, or four pulses to the mammalian cells at a field strength of 600-1,400 V/cm and a time constant from about 0.5 msec to about 10 msec to produce transfected mammalian cells.

2. The method of claim 1, wherein the transfection medium is an isotonic medium and a growth medium or a high conductance medium.

3. The method of claim 1, wherein a time between each pulse is between 1-15 seconds.

4. The method of claim 3, wherein the time between each pulse is between 2-10 seconds.

5. The method of claim 1, wherein the field strength is applied at a gap width of about 0.1 cm to about 0.4 cm.

6. The method of claim 1, wherein the time constant is about 0.5 msec to about 5 msec.

7. The method of claim 1, wherein the time constant is about 1 msec to about 3 msec.

8. The method of claim 1, wherein the field strength is applied at a voltage of between 150-250 V.

9. The method of claim 1, wherein the field strength is 800-1200 V/cm.

10. The method of claim 1, wherein the pulses are delivered from a capacitor having a capacitance of between 5-50 μF.

11. The method of claim 1, wherein the pulses are delivered from a capacitor having a capacitance of between 10-25 μF.

12. The method of claim 1, further comprising a step of culturing the transfected mammalian cells after pulsing.

13. The method of claim 1, wherein the transfected mammalian cells have a viability of at least 70%.

14. The method of claim 1, wherein the pulses provide a transfection efficiency of at least 80%.

15. The method of claim 1, wherein an injected charge is between 1 mC and 30 mC.

16. A method of transfecting mammalian cells with a RNA, comprising:

disposing the mammalian cells with the RNA in a transfection medium, wherein the mammalian cells are NK cells; and applying two, three, or four pulses to the mammalian cells at a voltage of 150-250 V, a gap width of about 0.1 cm to about 0.4 cm, and a time constant from about 0.5 msec to about 10 msec to produce transfected mammalian cells, wherein the pulses are delivered from a capacitor having a capacitance of between 5-50 μF.

17. A method of transfecting mammalian cells with a RNA, comprising:

disposing the mammalian cells with the RNA in a transfection medium, wherein the mammalian cells are NK cells; and applying two, three, or four pulses to the mammalian cells at a field strength of 600-1,400 V/cm and a time constant from about 0.5 msec to about 10 msec to produce transfected mammalian cells, wherein the pulses are delivered from a capacitor having a capacitance of between 5-50 μF.

* * * * *